(12) United States Patent
Jaeger

(10) Patent No.: US 8,800,090 B2
(45) Date of Patent: Aug. 12, 2014

(54) CLEANING APPARATUS

(76) Inventor: Anton Jaeger, Senden (DE)

( * ) Notice: Subject to any disclaimer, the term of this patent is extended or adjusted under 35 U.S.C. 154(b) by 168 days.

(21) Appl. No.: 13/273,312

(22) Filed: Oct. 14, 2011

(65) Prior Publication Data

US 2012/0090104 A1    Apr. 19, 2012

(30) Foreign Application Priority Data

Oct. 15, 2010 (DE) .......................... 10 2010 048 624

(51) Int. Cl.
| B08B 1/00 | (2006.01) |
| A61C 17/38 | (2006.01) |
| A61C 17/32 | (2006.01) |
| A61C 17/34 | (2006.01) |

(52) U.S. Cl.
CPC ................ *A61C 17/38* (2013.01); *A61C 17/32* (2013.01); *A61C 17/3445* (2013.01)
USPC .............................. 15/50.2; 15/49.1; 15/22.2

(58) Field of Classification Search
USPC ........ 15/22.1, 22.2, 23, 49.1, 50.1, 50.2, 160, 15/220.1, 103, 250.23
See application file for complete search history.

(56) References Cited

U.S. PATENT DOCUMENTS

| 2,559,295 A | 3/1951 | Grossenbacher |
| 3,056,151 A * | 10/1962 | Vlacancich .......................... 15/29 |
| 3,927,435 A * | 12/1975 | Moret et al. .................. 15/176.1 |
| 3,935,425 A | 1/1976 | Weissberger et al. |
| 4,163,302 A * | 8/1979 | Iaboni ............................. 15/50.1 |
| 8,024,995 B2 * | 9/2011 | Dayton et al. .................... 81/52 |
| 2004/0084063 A1 | 5/2004 | Vago et al. |

FOREIGN PATENT DOCUMENTS

| DE | 29 18 641 A1 | 11/1980 |
| DE | 33 42 374 A1 | 4/1984 |
| DE | 20 2008 016 815 U1 | 5/2009 |
| GB | 235 654 A | 6/1925 |

OTHER PUBLICATIONS

European Search Report dated Jul. 6, 2012 relating to EP Application No. 11 18 5292.
German Search Report dated Nov. 28, 2013 relating to DE Patent Application No. 10 2010 048 624.8.

* cited by examiner

*Primary Examiner* — Shay Karls
(74) *Attorney, Agent, or Firm* — Gifford, Krass, Sprinkle, Anderson & Citkowski, P.C.

(57) ABSTRACT

The invention relates to an apparatus, in particular to a cleaning apparatus, for carrying out a working movement moving to and fro, in particular a periodic working movement, in particular a cleaning movement, having a holding rod defining a longitudinal direction and a work unit which is coupled to the holding rod and which is movable relative to the holding rod for carrying out a working movement running parallel to the longitudinal direction, wherein an external drive is provided for generating the working movement.

34 Claims, 3 Drawing Sheets

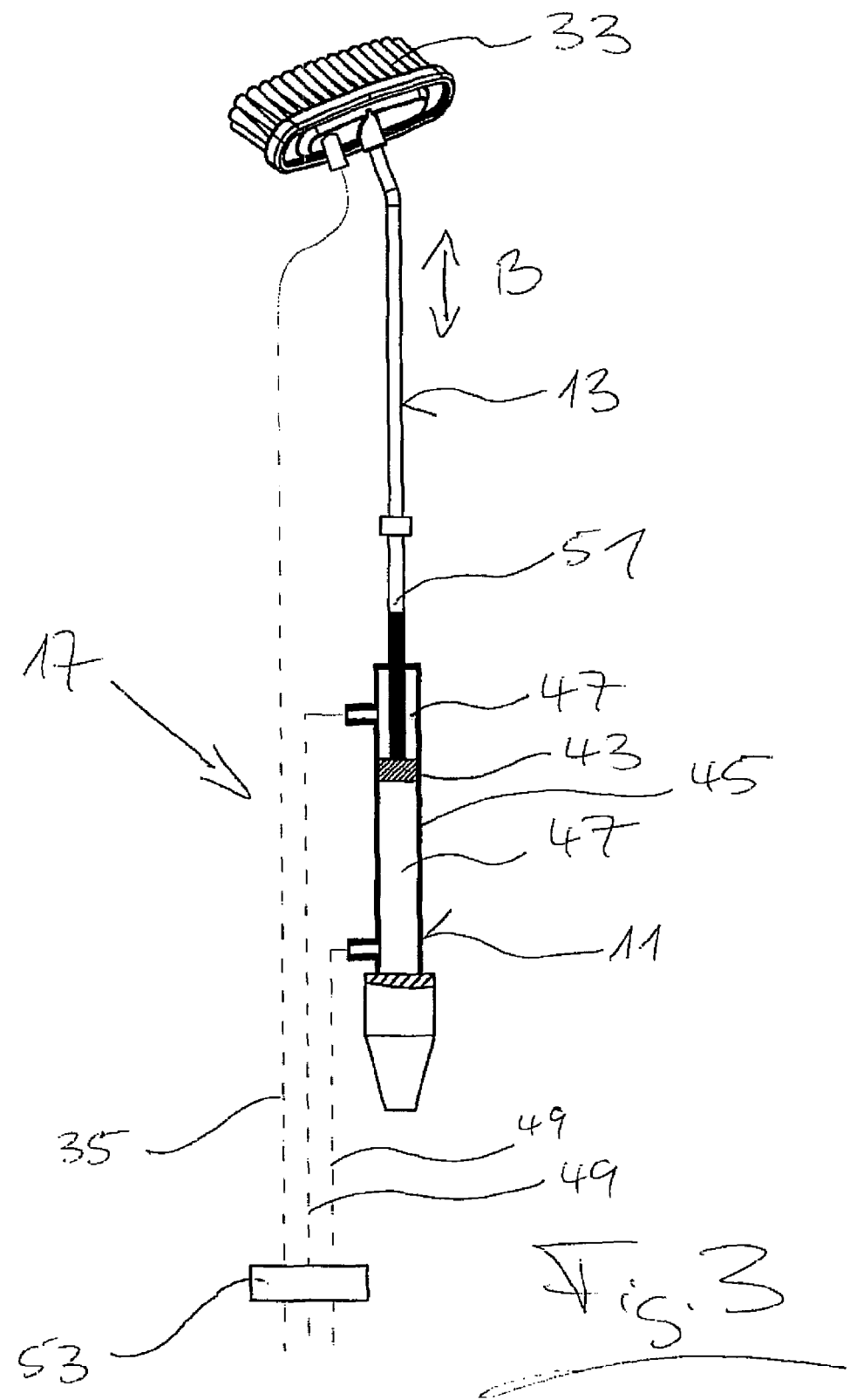

CLEANING APPARATUS

Figure 1:
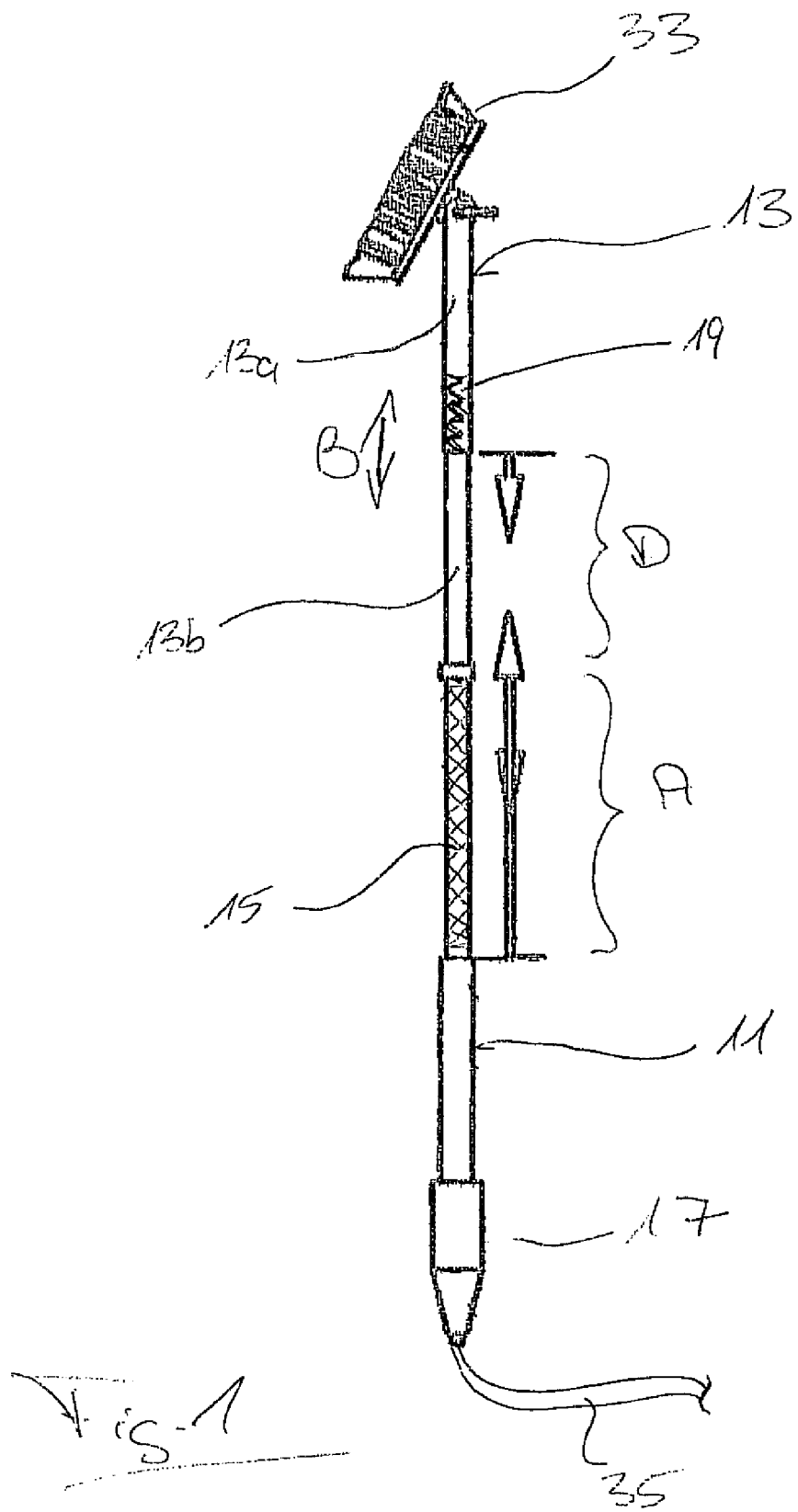

The invention relates to an apparatus, in particular to a cleaning apparatus, for carrying out a working movement moving to and fro, in particular a periodic working movement, in particular a cleaning movement.

It is known to attach a cleaning member, e.g. a washing brush, to the end of a telescopic rod or of a rod of unchanging length for the treatment, e.g. for the cleaning, of otherwise inaccessible areas, for example for the purpose of cleaning windows at residential properties. To achieve a to-and-fro movement of the cleaning member advantageous in particular for cleaning purposes, the user must constantly move the cleaning member up and down together with the rod and any possibly present water line for the supply of water to the cleaning member. Depending on the design of the apparatus, this is associated with substantial physical effort so that such cleaning apparatus are unsuitable for use of longer duration.

It is the object of the invention to improve an apparatus of the initially named kind such that its use is also possible over a relatively long period, in particular with respect to the force effort to be applied.

In accordance with the invention, the apparatus includes a holding rod defining a longitudinal direction as well as a work unit which is coupled to the holding rod and which is movable relative to the holding rod for carrying out the working movement running parallel to the longitudinal direction, with an external drive in particular being provided for generating the working movement. A motor drive, a fluid drive, a pneumatic drive or a hydraulic drive can e.g. be provided as the external drive.

Since, in accordance with the invention, the work unit is movable relative to the holding rod, it is not necessary for the carrying out of the working movement to move the holding rod up and down together with the work unit, that is to move the total apparatus.

If an external drive is provided for generating the working movement, that is if the user does not have to produce the working movement himself by muscle power, the work of the user is restricted to the holding of the apparatus, i.e. neither a movement up and down of the total apparatus nor a movement to and fro of the work unit relative to the holding rod has to be carried out by the user himself. An external drive is therefore advantageous, but not mandatory in accordance with the invention.

Further preferred embodiments of the invention are set forth in the dependent claims, in the description and in the drawing.

Provision can be made that the work unit is coupled to a spindle extending in the longitudinal direction and drivable to make a rotation such that a rotational movement of the spindle can be converted into the working movement.

In this respect, the relative movement between the work unit and the holding rod is achieved by means of a spindle which can be set into rotation so that only a rotation of the spindle has to be provided to be able to move the work unit to and fro parallel to the longitudinal direction of the holding rod.

It is thus conceivable in principle, for example, that the user sets the spindle into rotation himself by hand, for example by means of a crank mechanism. This is above all possible in practice because not the total holding rod together with the work unit has to be moved, but only the lighter work unit. It is, however, to be preferred if the rotational drive for the spindle does not have to be applied by the user. It is in particular possible in accordance with the invention to use an external drive, in particular a fluid drive or a motor drive, for the spindle, which will be looked at in more detail in the following.

In a further embodiment, the spindle can be driven to make a rotational movement having a single sense of rotation. The work unit in particular cooperates with the spindle such that a rotational movement having a single sense of rotation can be converted into opposite components of the working movement. Such an embodiment is above all of advantage when a drive is selected for the spindle with which it is not possible or not desired—at least with a justifiable construction effort and/or economic effort—to provide a switchover between the two rotational directions of the spindle.

In a preferred embodiment, the spindle is designed as a reversing spindle, a reversal spindle, a cross-spindle or a cross-threaded spindle. Such spindles are known in the general field of winding, for example in connection with cable spools, cable pulleys and fishing reels. The advantage of these spindles is that they only need to rotate in one direction. The extent of the achievable working movement, i.e. the "movement path" or "stroke" achievable along the spindle axis, is in this respect defined by the effective length of the spindle, i.e. by the axial length of the thread.

A fluid drive is provided for the spindle in a further embodiment of the invention. The fluid drive is in particular designed to convert the flow energy of a fluid supplied under pressure into the rotational movement of the spindle.

The fluid drive can have at least one drive member, in particular a turbine or a bucket wheel, which is directly driven by the fluid and by which the spindle can be driven.

Such fluid drives can be manufactured extremely inexpensively and work very reliably, with sufficiently high torques as well as sufficiently high speeds of rotation also being able to be achieved when the fluid drive is connected to a conventional high-pressure cleaner such as is available to private persons everywhere. A fluid drive can then be designed particularly simply and manufactured inexpensively if no switchover possibility is required for a change of the direction of rotation of the spindle so that the above-mentioned design of the spindle e.g. as a cross-threaded spindle in connection with a fluid drive is particularly advantageous.

The fluid drive can include a transmission unit having an inlet acted on by fluid at the drive member and an outlet cooperating with the spindle. In this manner, the required torque ratios and speed of rotation ratios at the spindle can be set in dependence on the available fluid pressure and on the supplied fluid quantity.

It is also possible to drive the spindles by a motor, for example by means of an electric motor. In this case, the spindle can be designed, for example, as a ball screw spindle. In this respect, a switchover possibility is required between the directions of rotation of the spindle, which is, however, not problematic in connection e.g. with an electric motor. The adjustment path in the longitudinal direction can be kept variable in this manner. Such an arrangement can, for example, be provided with an end position detection. Equally, different programs can be defined which, for example, selectively allow a short-stroke operation and a long-stroke operation.

In a further embodiment, a pneumatic drive or a hydraulic drive is provided for generating the working movement, with in particular the work unit being coupled to a piston which is movable to and fro in a cylinder by coordinated application of a medium from at least two chambers separated from one another by the piston.

In a further embodiment of the invention, an overload protection device is provided for external forces acing on the work unit and acting against the working movement. This is, for example, of advantage when the there is a risk that, on an upward movement, that is with a movement of the work unit resulting in an extension of the total apparatus, said work unit impacts obstacles at the object to be cleaned. The overload protection device can ensure that the external drive, in particular the spindle or the piston, is not damaged in an overload situation.

The overload protection device can include a buffer and/or a spring device or damping device which is effective between the work unit and the external drive, in particular the spindle or the piston.

Alternatively or additionally, the overload protection device can be designed in the manner of a safety coupling.

In a preferred embodiment in which the spindle is designed as a reversing spindle, a reversal spindle, a cross spindle or as a cross-threaded spindle, the overload protection device is integrated into a cam guide which is active between the spindle and the work unit and which converts the rotational movement of the spindle into the working movement of the work unit. In this respect, the cam guide is designed such that at least one guide element engaging into a slotted link of the spindle first moves out of the engagement with the slotted link in an overload situation and subsequently moves back into engagement with the slotted link at a point spaced apart in the longitudinal direction. The guide element formed, for example, as a link block can be prestressed into the slotted link of the spindle by e.g. a spring so that it is pressed out of the slotted link, for example, due to a suitably arranged and designed slope when the spindle and the link block are moved toward one another parallel to the longitudinal direction, such as is the case when the work unit impacts an obstacle. The special advantage of this overload protection device is that the guide element can automatically spring back into the slotted link, and indeed in a relative position between the spindle and the work unit in which the work unit no longer cooperates with the obstacle. The user consequently does not need to take any measures to set the apparatus back into motion after an overload situation. This embodiment of the invention therefore not only provides a fully automatic overload protection, but also a practically delay-free fully automatic restart of the working operation subsequent to an overload situation.

Provision can furthermore be made in accordance with the invention that a security against rotation is provided for the work unit which prevents a rotation of the work unit with the spindle. The security against rotation can be active between the work unit, in particular a sleeve part surrounding the spindle, and a reception part, in particular an external reception tube, rotationally fixed with respect to the spindle. The security against rotation can include a compulsory guide extending parallel to the longitudinal direction between the work unit and the reception part.

To increase the stability of the apparatus in accordance with the invention and in particular to prevent a lateral migration of the spindles in the region of its free end, provision can be made that the spindle is guided and/or supported at least in the region of its end facing the work unit by means of a reception part, in particular an external reception tube, and/or by means of the work unit, in particular a sleeve part surrounding the spindle.

It is preferred if the fluid used for a fluid drive of the spindle is subsequently supplied to the work unit in order in this manner to achieve a double use of the fluid. The fluid can be conducted from the drive unit to the work unit via an internal line of the apparatus and/or via an externally disposed line.

Figure 2:
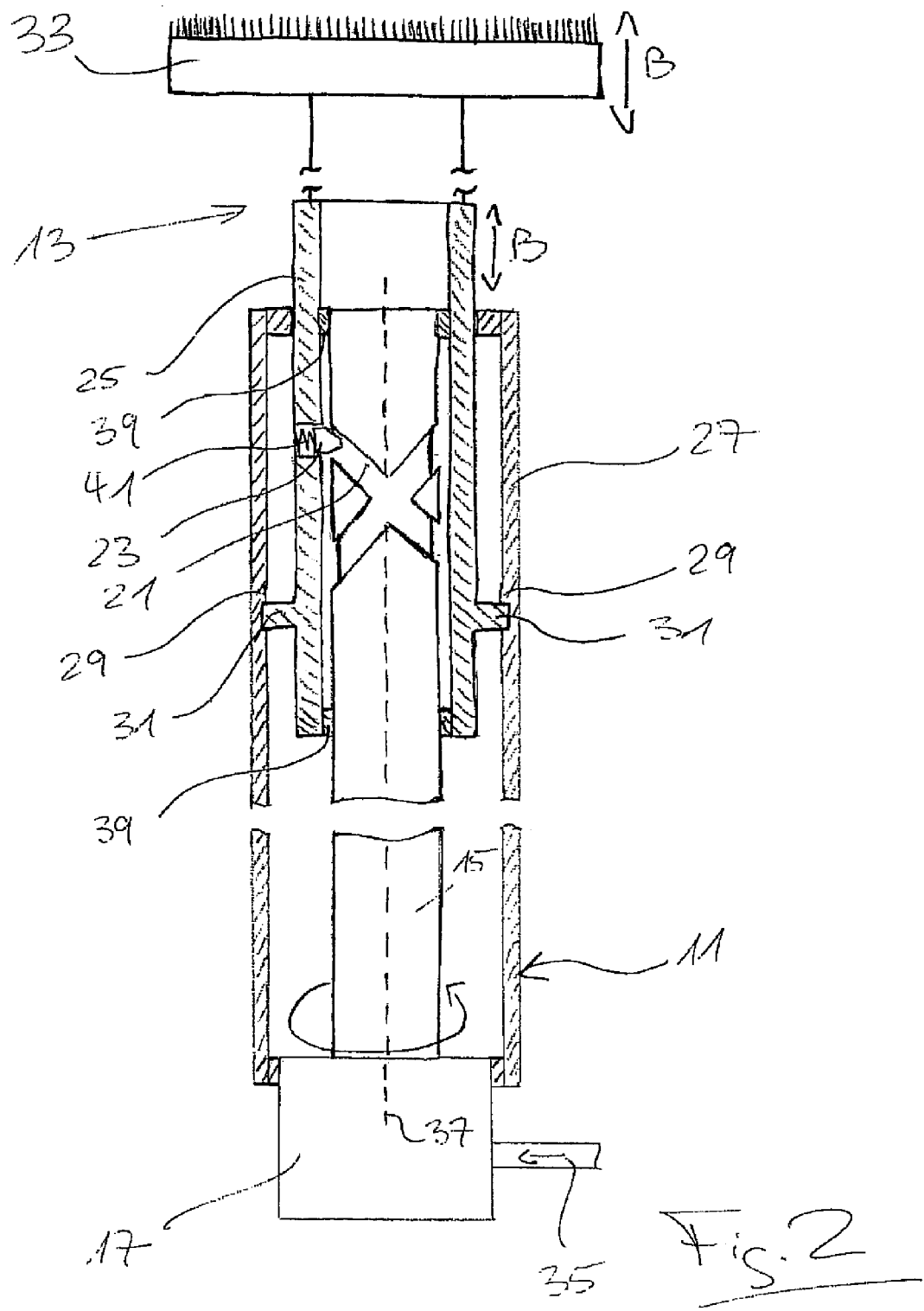

The invention will be described in the following by way of example with reference to the drawing. There are shown:

FIG. 1 schematically, an embodiment of an apparatus in accordance with the invention;

FIG. 2 schematically an apparatus in accordance with the invention in accordance with a further embodiment; and FIG. 3 schematically an apparatus in accordance with the invention in accordance with a further embodiment.

FIG. 1 shows a cleaning apparatus in accordance with the invention which has an elongated structure, with a work unit 13 having a cleaning brush 33 being attached to the one end and with a supply line 35 being connected to the other end via which a fluid, in particular water, can be supplied under pressure to the cleaning apparatus, for example by a conventional high-pressure cleaner.

The apparatus is only shown schematically and partially here. A holding rod 11 at which a user can hold the apparatus with his hand actually extends up to the height of the work unit 13 and receives the components described in the following in itself.

The apparatus is provided with a cross-threaded spindle 15 which is rotatably supported about an axis extending parallel to the longitudinal extent of the apparatus. To set the spindle 15 into rotation, a drive unit 17 is provided which will not be looked at in any more detail at this point. The drive unit 17 can, for example, be a fluid drive or a motor drive.

The work unit 13 in this embodiment includes a front section 13a which carries the cleaning brush 33 and a rear part 13b which cooperates with the spindle 15. A spring 19 is located between the two sections 13a, 13b of the work unit 13 and acts as a buffer or overload protection device such as was described in the introduction part. If the cleaning brush 33 impacts an obstacle on an upward movement, the length of the work unit 13 shortens due to the compression of the spring 19 so that this overload situation does not result in damage in the region of the coupling between the work unit 13 and the spindle 15. The damping region D hereby present in the longitudinal direction is indicated schematically in FIG. 1.

As already presented generally in the introduction part, the rotational movement of the spindle 15 is converted into a periodic up-and-down movement or to-and-fro movement (working movement B) of the work unit 13 relative to the spindle 15 and thus to the holding rod 11, as is indicated by the double arrow. Guided by the thread of the spindle 15, the work unit 13 moves up and down during a rotational movement of the spindle 15 always taking place with one sense of rotation, with the stroke length being determined by the axial length of the spindle thread. This travel path is available as a working stroke and is indicated as working region A in FIG. 1. The apparatus is therefore shown with a maximally extended work unit 13 in FIG. 1.

The fluid, in particular water, supplied via the line 35 can be supplied to the cleaning brush 33, for example via a line, not shown, for example a hose, which runs centrally through the apparatus, e.g. also while including the spindle 15. It is alternatively or additionally possible to supply the fluid via an outwardly disposed line.

If the drive 17 for the rotational movement of the spindle 15 is a fluid drive, the fluid providing the rotary drive of the spindle 15 can subsequently be supplied to the cleaning brush 33 in a suitable manner in order to be used twice in this manner.

In the embodiment of FIG. 2, the cleaning apparatus includes a fluid drive 17 to which the pressurized water delivered, for example, from a connected high-pressure cleaner can be supplied via a line 35 and which can set a cross-threaded spindle 15 into rotation about an axis of rotation 37.

In its upper region, the spindle 15 carries a sleeve part 25 of a work unit 13 which additionally includes a cleaning brush 33 connected to the sleeve part 25.

The sleeve part 25 is provided with a guide element 23 in the form of a sliding block which projects at its inner side and which engages into the thread of the spindle 15 acting as a slotted link 21; only some of the thread turns of the thread are indicated here.

When the spindle 15 rotates, the cam guide formed by the slotted link 21 and the sliding block 23 provides that the sleeve part 25, and thus the total work unit 13 together with the cleaning brush 33, moves to and fro along the spindle 15, with the design of the end regions of the spindle thread not shown here providing the reversal of direction at the upper end and at the lower end of the spindle 15.

A rotation of the sleeve part 25, and thus of the work unit 13, with the spindle 15 is prevented in that the sleeve part 23 is rotationally fixedly guided with a reception part 27 in the form of an external reception tube via a compulsory guide extending along the axis of rotation 37. The compulsory guide is formed by projections 31 at the outer side of the sleeve part 25 and slots 29 in the reception tube 27. The external tube 27 simultaneously forms the holding rod 11 for the user.

This arrangement is given stability by a suitable guiding or support of the spindle 15. This is indicated schematically in FIG. 2. The spindle 15 is guided at least at its upper end by a slide guide 39 formed at the inner side of the sleeve part 25.

A special feature of this embodiment is represented by the overload protection device which was already addressed in the introduction part and which is here integrated into the cam guide comprising the slotted link 21 of the spindle 15 and the sliding block 23 of the sleeve part 25. The sliding block 23 is prestressed into the slotted link 21 by means of a spring 41. The sliding block 23 can therefore move out of engagement with the slotted link 31 against the restoring force of this spring 41 when external forces effect an axial relative movement between the spindle 15 and the sleeve part 25. This is in particular the case when the cleaning brush 33 impacts an obstacle on a movement in the sense of an extension of the total apparatus. In this respect the sliding block 23 is pressed out of the slotted link 21 due to a slope formed at the sliding block 23 so that the arrangement of sleeve part 25 and spindle 15 can be shortened. When the sliding block 23 in so doing reaches the next turn of the slotted link 21, the sliding block 23 jumps back into the slotted link 21, whereupon the working movement B is immediately continued due to the still rotating spindle 15.

The water supply to the cleaning brush 33 is not shown in FIG. 2. The water can be supplied inside the reception tube 27, for example through the spindle 15, with it alternatively being possible to supply the water via a line laid outside the reception tube 27.

The design of the fluid drive 17 for the rotation of the spindle 15 is generally any desired so that it is not necessary to look into this in any more detail. Such fluid drives are generally known. The fluid drive 17 in particular includes as an inlet part a drive member which is designed as a turbine or as a bucket wheel which is acted on directly by the fluid supplied via the line 35 and in this manner sets an outlet part into rotation which is connected to the spindle 15 via a transmission.

A pneumatic or hydraulic drive is provided as an external drive 17 for the work unit 13 in the embodiment of FIG. 3. The work unit 13 includes a piston rod 51 which is connected to a piston 43. The piston 43 is movable to and fro in a cylinder 45. The cylinder 45 can serve as a holding rod 11, with this, however, not being compulsory. The length of the cylinder 45 or of the holding rod 11 can also be selected larger, as is shown in FIG. 3. It is also possible that a section, not shown here, adjoins the end of the cylinder 45 remote from the work unit 13, said section serving as a holding rod or as an extension of the holding rod formed by the cylinder 45.

In the embodiment shown, the cylinder 45 includes two chambers 47 which are disposed on opposite sides of the piston 43. Since the two chambers 47 are acted on in a suitable manner by a medium, for example compressed air, the piston 43 can be moved to and fro in the cylinder 45. This external drive for the work unit 13 is controlled by a control 53 which is indicated only schematically in FIG. 3 and to which the control lines 49 are connected.

A fluid line 35 with which a cleaning fluid, in particular water, is supplied to the cleaning brush 33 provided at the work unit 13, is likewise connected to the control 53.

An overload protection can also be integrated in this embodiment of the invention, for example in the form of a spring or of a damper which is effective in a suitable manner between the work unit 13 and e.g. the cylinder 45.

REFERENCE NUMERAL LIST 11 holding rod
13 work unit
13a front section
13b rear section
15 spindle
17 external drive, fluid drive, pneumatic drive
19 damping spring
21 slotted link, spindle thread
23 guide element, sliding block
25 sleeve part
27 reception part, external reception tube
29 slot
31 projection
33 cleaning brush
35 supply line
37 axis of rotation
39 slide guide
41 spring
43 piston
45 cylinder
47 chamber
49 control line
51 piston rod
53 control
B working movement
D damping region
A working region

The invention claimed is:

1. An apparatus for carrying out a working movement (B) moving to and fro having an elongated holding rod (11) defining a longitudinal direction and a work unit (13) which is coupled to the holding rod (11) and which is movable linearly only in said longitudinal direction relative to the holding rod (11) for carrying out the working movement (B) running parallel to the longitudinal direction, wherein an external drive (17) is provided for generating the working movement (B) wherein longitudinal movement of said work unit relative to said holding rod changes an overall length of the apparatus in said longitudinal direction, wherein the work unit (13) is coupled to a spindle (15) extending in the longitudinal direction and drivable to make a rotation such that a rotational movement of the spindle (15) can be converted into the working movement (B).

2. An apparatus in accordance with claim 1, wherein said apparatus is a cleaning apparatus.

3. An apparatus in accordance with claim 1, wherein said working movement is a periodic working movement.

4. An apparatus in accordance with claim 1, wherein said working movement is a cleaning movement.

5. An apparatus in accordance with claim 1, wherein the spindle (15) can be driven to make a rotational movement having a single sense of rotation, and/or
wherein the work unit (13) cooperates with the spindle (15) such that a rotational movement having a single sense of rotation can be converted into opposite components of the working movement (B).

6. An apparatus in accordance with claim 1, wherein the spindle (15) is designed as a reversing spindle, reversal spindle, cross spindle or crossed-thread spindle.

7. An apparatus in accordance with claim 1, wherein a fluid drive (17) is provided for the spindle (15),
with the fluid drive (17) being designed to convert the flow energy of a fluid supplied under pressure into the rotational movement of the spindle (15).

8. An apparatus in accordance with claim 7, wherein the fluid drive (17) includes a transmission unit having an inlet acted on by fluid at the drive member and an outlet cooperating with the spindle (15).

9. An apparatus in accordance with claim 7, wherein the fluid drive (17) has at least one drive member which is directly driven by the fluid and by which the spindle (15) can be driven.

10. An apparatus in accordance with claim 9, wherein said drive member is a turbine or a bucket wheel.

11. An apparatus in accordance with claim 1, wherein the spindle (15) can be driven to make opposite rotational movements, with a first rotational movement being able to be converted into a first component of the working movement (B) and a second rotational movement opposite to the first rotational movement being able to be converted into a second component of the working movement (B) opposite the first component.

12. An apparatus in accordance with claim 11, wherein the spindle (15) can be driven by a motor.

13. An apparatus in accordance with claim 11, wherein the spindle (15) can be driven by means of an electric motor.

14. An apparatus in accordance with claim 11, wherein the spindle (15) is made as a ball screw spindle.

15. An apparatus in accordance with claim 1, wherein an overload protection device is provided for external forces acting on the work unit (13) and opposite to the working movement (B).

16. An apparatus in accordance with claim 15, wherein the overload protection device includes a spring device or damping device (19) which is active between the work unit (13) and the external drive (17).

17. An apparatus in accordance with claim 16, wherein the overload protection device is active between work unit and the spindle (15) or between the work unit and a piston.

18. An apparatus in accordance with claim 15, wherein the overload protection device is designed in the manner of a safety coupling.

19. An apparatus in accordance with claim 15, wherein the overload protection device is integrated into a cam guide (21, 23) which is active between the spindle (15) and the work unit (13), which converts the rotational movement of the spindle (15) into the working movement (B) of the work unit (13) and which is designed such that at least one guide element (23) engaging into a slotted link (21) of the spindle (15) first moves out of engagement with the slotted link (21) in an overload situation and subsequently moves back into engagement with the slotted link (21) at a point spaced part in the longitudinal direction.

20. An apparatus in accordance with claim 19, wherein said spindle is formed as a reversing spindle, a reversal spindle, a cross spindle or a crossed-thread spindle.

21. An apparatus in accordance with claim 1, wherein a security against rotation is provided for the work unit (13) which prevents a rotation of the work unit (13) and which is effective between the work unit (13) and a rotationally fixed reception part (27).

22. An apparatus in accordance with claim 21, wherein said security against rotation is a sleeve part (25) surrounding the spindle (15) and/or wherein said rotationally fixed reception part is an external reception tube.

23. An apparatus in accordance with claim 21, wherein
the security against rotation includes a compulsory guide (29, 31) running parallel to the longitudinal direction between the work unit (13) and the reception part (27).

24. An apparatus in accordance with claim 1, wherein the spindle (15) or the piston (43) is guided at least in the region of its end facing the work unit (13) by means of a reception part (27), and/or by means of the work unit (13).

25. An apparatus in accordance with claim 24, wherein said reception part is an external reception tube.

26. An apparatus in accordance with claim 24, wherein said work unit (13) comprises a sleeve part (25) surrounding the spindle (15) or a piston (43).

27. An apparatus for carrying out a working movement (B) moving to and fro having an elongated holding rod (11) defining a longitudinal direction and a work unit (13) which is coupled to the holding rod (11) and which is movable linearly only in said longitudinal direction relative to the holding rod (11) for carrying out the working movement (B) running parallel to the longitudinal direction, wherein an external drive (17) is provided for generating the working movement (B) wherein longitudinal movement of said work unit relative to said holding rod changes an overall length of the apparatus in said longitudinal direction,
wherein said working movement is a periodic working movement, wherein
a pneumatic drive or a hydraulic drive (17) is provided for generating the working movement (B),
with the working unit (13) being coupled to a piston (43) which is movable to and fro in a cylinder (45) by coordinated application of a medium from at least two chambers (47) separated from one another by the piston (43).

28. An apparatus in accordance with claim 27, wherein said apparatus is a cleaning apparatus.

29. An apparatus in accordance with claim 27, wherein
an overload protection device is provided for external forces acting on the work unit (13) and opposite to the working movement (B).

30. An apparatus in accordance with claim 29, wherein
the overload protection device includes a spring device or damping device (19) which is active between the work unit (13) and the external drive (17).

31. An apparatus in accordance with claim 30, wherein the overload protection device is active between work unit and the spindle (15) or between the work unit and a piston.

32. An apparatus in accordance with claim 27, wherein a security against rotation is provided for the work unit (13)

which prevents a rotation of the work unit (13) and which is effective between the work unit (13) and a rotationally fixed reception part (27).

33. An apparatus in accordance with claim 32, wherein said security against rotation is a sleeve part (25) surrounding the spindle (15) and/or wherein said rotationally fixed reception part is an external reception tube.

34. An apparatus in accordance with claim 32, wherein the security against rotation includes a compulsory guide (29, 31) running parallel to the longitudinal direction between the work unit (13) and the reception part (27).

* * * * *